United States Patent [19]

Brookfield

[11] Patent Number: 5,535,619
[45] Date of Patent: Jul. 16, 1996

[54] PRESSURIZED VISCOMETER

[75] Inventor: David A. Brookfield, Sharon, Mass.

[73] Assignee: Brookfield Engineering Laboratories, Inc., Stoughton, Mass.

[21] Appl. No.: 341,498

[22] Filed: Nov. 17, 1994

[51] Int. Cl.$^6$ .................................................. G01N 11/140
[52] U.S. Cl. ........................................ 73/54.33; 73/54.35
[58] Field of Search ............................... 73/54.01, 54.14, 73/54.16, 54.28, 54.31, 54.32, 54.33, 54.34, 54.37, 54.43, 54.35

[56] References Cited

U.S. PATENT DOCUMENTS

| | | | |
|---|---|---|---|
| 2,027,903 | 1/1936 | Dintilhac | 73/54.28 |
| 2,553,844 | 5/1951 | Buchdahl et al. | 73/54.28 |
| 2,643,543 | 6/1953 | Herzog | 73/54.34 |
| 2,660,885 | 12/1953 | Evans | 73/54.28 |
| 3,435,666 | 4/1969 | Fann | 73/54.39 |
| 3,886,789 | 6/1975 | Brookfield | 73/59 |
| 4,175,425 | 11/1979 | Brookfield | 73/59 |
| 4,448,061 | 5/1984 | Brookfield | 73/59 |
| 4,571,988 | 2/1986 | Murphy | 73/54.33 |
| 5,167,143 | 12/1992 | Brookfield | 73/54.23 |

OTHER PUBLICATIONS

Title: Apparatus for Studying the Rheological Behavior of Carbonaceous Materials at Elevated Temperature and Pressure. Authors: Garratt, G. W.; Rand, B.; Whitehouse, S. Source: Fuel v 67 N 2 Feb. 1988 pp. 238–241.

Title: Portable High–Temperature, High–Pressure Viscometer Development. Authors: Reineke, R. C., Sandia Labs., Albuquerque, N.M. Source NTIS Accession Number: SAND–78–1409.

*Primary Examiner*—Hezron E. Williams
*Assistant Examiner*—Jay L. Politzer
*Attorney, Agent, or Firm*—Jerry Cohen

[57] ABSTRACT

Pressurized viscometer (10) with fluid holder (12) rotatable by a motor (M) and gearing (50) to shear a tested fluid F thus imparting torque to a spindle assembly 32 mounted via a flexural mount (rods TR) and having a read-out rod or wire (40) with an adjacent transducer (R, S), the wire passing through an elongated holder shaft (18) within a fixed cylinder that mounts an elongated fluid holder extension (16) via an elongated bearing array (20, 24) on the outer surface thereof.

4 Claims, 2 Drawing Sheets

5,535,619

PRESSURIZED VISCOMETER

BACKGROUND OF THE INVENTION

The present invention relates to measurement of viscosity with a variable speed drive.

The state of the art of viscometry involves a calibrated application of shear force to a fluid to be tested and measuring torque and/or time-to-torque of the shear resistance of the fluid (its viscosity). See e.g., prior U.S. Pat. No. 3,886,789 (Jun. 3, 1975) of Donald W. Brookfield and U.S. Pat. No. 4,175,425 (Nov. 27, 1979) and U.S. Pat. No. 5167143 (Dec. 1, 1992) of David A. Brookfield, all of common assignment with the present application. See also, references cited in said prior patents.

It is an object of this invention to provide a reliable, but rugged instrument usable in quick change (test set ups) viscosity measuring applications, under pressurized and high temperature conditions.

SUMMARY OF THE INVENTION

The present invention is a pressurized rotary viscometer with means defining a fluid containing housing of cup form (i.e. to hold the fluid to be tested), a spindle therein, a variable speed motor for driving the housing, means to pressurize the housing, a spindle mount that includes an elongated torsion element wire for read out within a sealing tube, a torque transducer arranged to respond to torque loading of the wire, means to pressurize a work space in the housing to isolate the wire and to isolate the housing, the latter isolation means having a bearing and seal system.

Other objects, features and advantages will be apparent from the following detailed description of preferred embodiments taken in conjunction with the accompanying drawings in which:

DETAILED DESCRIPTION OF PREFERRED EMBODIMENTS

Figure 1:
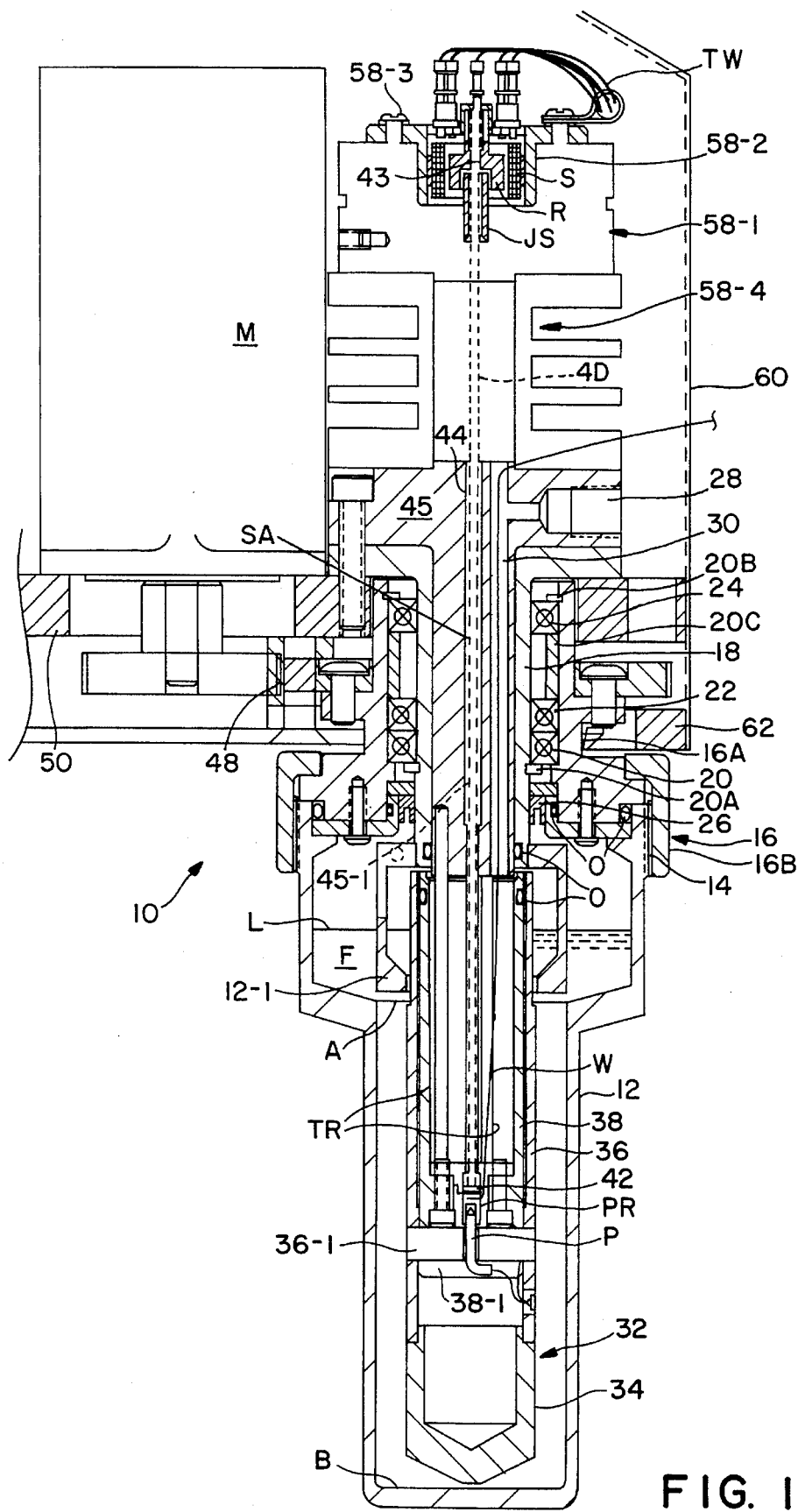
FIG. 1 is a cross-section view of a preferred embodiment of the invention.

FIG. 1 shows a viscometer 10 with a cup 12 for fluids and a cup holder and alignment assembly 16. The alignment assembly is rotatable about a fixed load-bearing sleeve shaft assembly 18. The latter contains concentrically within it a sensing assembly SA which has no torque imparted to or from the sleeve and a shaft 45 supported via axially spaced bearings 20, 22, 24 with bearing retainer rings 20A, 20B and a bearing loading spacer 20C. Two spaced bearings 20 and 24 are needed for alignment. Addition of a further bearing 22 helps to resist pressure loading. The cup is detachable from a cup holder end 16B (mounted on a cylindrical shaft 16A of assembly 16) via screw threads 14. A rotary seal 26 mounted on the cup holder end of shaft 16A isolates the bearings from fluids being measured and functions at rotational sliding rates from 0.005 rpm to 1,500 rpm. A pressure port 28 and line 30, passing through the sensing assembly, provides means for pressurizing the interior of the viscometer with gas from an external source (not shown). Pressurization limits volatility of the fluid being measured and also limits fluid splash or upward creep.

A spindle assembly 32 is mounted in the cup and comprises a spindle cap 34 welded to an outer sleeve 36 and a cross pin 36-1. Sleeve 36 slides on to an alignment tube 38 and is held thereto by a spring clip (not shown). This assures alignment of spindle 32.

A read out wire 40 is fixed at 42 to the end of the torsion element which twists with the spindle assembly through an arc of not more than one degree down to as low as 0.05 degrees full scale. The wire at its upper end 43 ties to a rotor R after passing through a rigid jewel support JS which affords radial locking but allows rotation. The transducer rotor R and stator S comprise an industry standard electromagnetic (microsyn) pickup. The wire passes through an axial hole 44 in a torsion assembly shaft 45.

A motor M drives the cup and holder (12, 16) via gearing 48. The motor and gearing are mounted on fixed chassis structure 50 of the instrument.

Motor M is typically a stepper motor or variable speed motor sufficient to drive against axial loads due to pressure. The motor drives the cup 12 via a gearing (48) ratio of between 1:1 to 4:1, to a speed in the range of 0.005 to 3,000 rpm. Shear forces transmitted via the fluid under test (indicated at F) are created by the cup. As noted above, the cup is screwed to the holder 16 via threads 14. The interior zone F may be gas pressurized to about 1,000 psi via 28, 30). The shear force transmission drives the spindle 32 to partially rotate wire 40 in an arc measurable at transducer S/R (less than one degree variation).

A temperature pickup T (which can be a thermostat or other temperature responsive sensor) connects, via a wire W and ground of the instrument as a whole to an external control. Circuit transducer wires TW also lead to the external control. The signal path includes a pin P and pin receptacle PR which is dielectrically isolated from its support structure in the instrument.

The general surround structure of holder assembly 16, the rotary seal 26 and O-rings O assure against gas escapes and/or escape of tested fluid. The lowermost of such rings (between tubes 36, 38) guards against measured liquid, volatile derivatives or pressurized gas penetration between those tubes.

The fluid level is indicated at L. Penetration of splash or creep of such fluid into upper structure or within the torsion assembly must be avoided. In addition there must be room within the housing to allow for fluid thermal expansion (as it is heated by the usual thermal bath around the housing and the heating due to working the fluid) without permitting overflow into the torsion assembly or outflow from the measurement zone via the pressure port. Pressurization assists in this regard (as well as controlling evaporation of volatiles of fluid F and avoiding boiling and foaming and consequent viscosity changes). A baffle ring 12-1 is mounted closely (about 1/16" clearance) to the top A of the measurement zone (extending from A to B) to limit fluid outflow from the zone under high speed rotation and consequent centrifugal forces. The baffle also limits spurious sensing of the upper portion of the spindle extension above the measuring zone. The baffle is attached to the fixed shaft 18 and does not contribute torque to the sensing elements.

The fixed upper structure includes a transducer housing 58-1 with a zero adjust ring 58-2 (for adjustable mounting of the transducer stator to vary its field position to reach a null output; adjusting is done manually, rotationally, after loosening screws 58-3, to establish the sensing range). It also includes a ribbed temperature stand-off spacer 58-4 that substantially isolates the transducer from thermal conditions of the measuring zone.

Shaft 18 has an integral flange that is clamped between a base plate fixed structure 50 and an integral flange of the torsion assembly's shaft 45.

The torsion assembly has three rods TR as in state-of-the-art TT brand instruments (Brookfield Engineering Laboratories, Inc.). A sealing tube SW, sealed into assembly 45 at 45-1, surrounds the read-out wire 40. The tube is also sealed at 42. The spindle extension tube 36 has a mounting bar 36-1, slips into a slot 38-1 of alignment tube 38 and is locked therein by a spring (not shown). A pin P passes through a hole in the mounting bar, and accommodates wire W of temperature probe T. The pin P engages a pin receptacle PR which transfers a live signal (not ground) to an upper section of wire W.

Figure 1A:
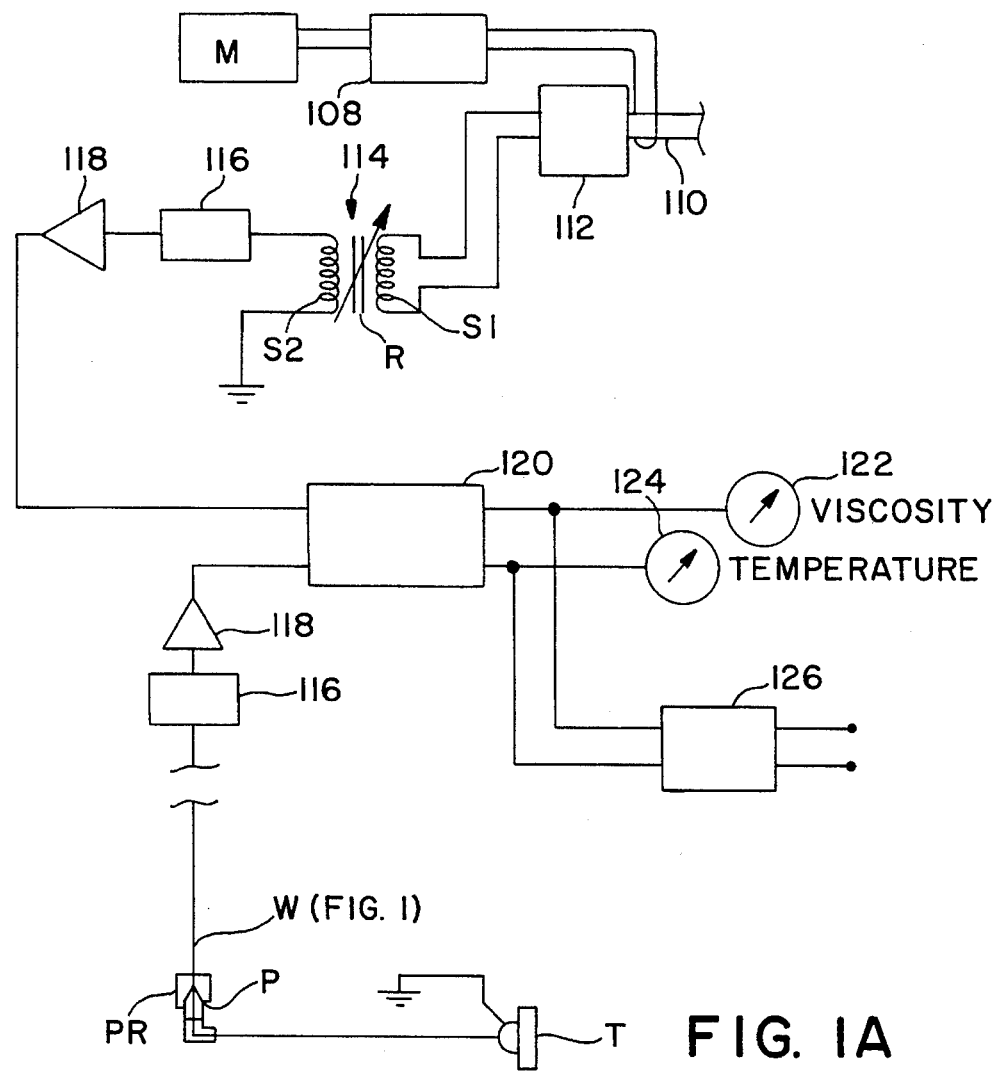
FIG. 1A is a schematic representation of the electrical system therein.

FIG. 1A shows the basic electrical circuit of the instrument including a power cord 110, driving power supply 108 for motor M (FIG. 1) and a further power supply section 112 for the transducer which, as mentioned above, comprises a stator and rotor. The stator is a transformer of concentrically or side-by-side wound primary (S1) and secondary coils (S2). The rotor R mounted to wire 40 (FIG. 1) for angular deflection therewith (in a range of about 0.05 to 1.0 degrees) is a magnetic material arranged as the transformer core, all in a manner well known in the art. The special radial jewel mounting of wire 40 at JS (FIG. 1) from fixed structure 58-1, is essentially free of axial drag or friction, as noted above. The thermal, vibrational and extraneous torque (apart from the torque on read-out wire 40 to be measured) isolation of the transducer from the measuring zone is also important. A demodulator 116, amplifier 118 and signal output processor 120 supply the signal in properly conditioned form to readout devices (122 for viscosity, 124 for temperature readings of probe T (FIG. 1) also transmitted via processor 120) and/or to a programmable controller or computer 126 for process control and/or data accumulation.

Figure 1B:
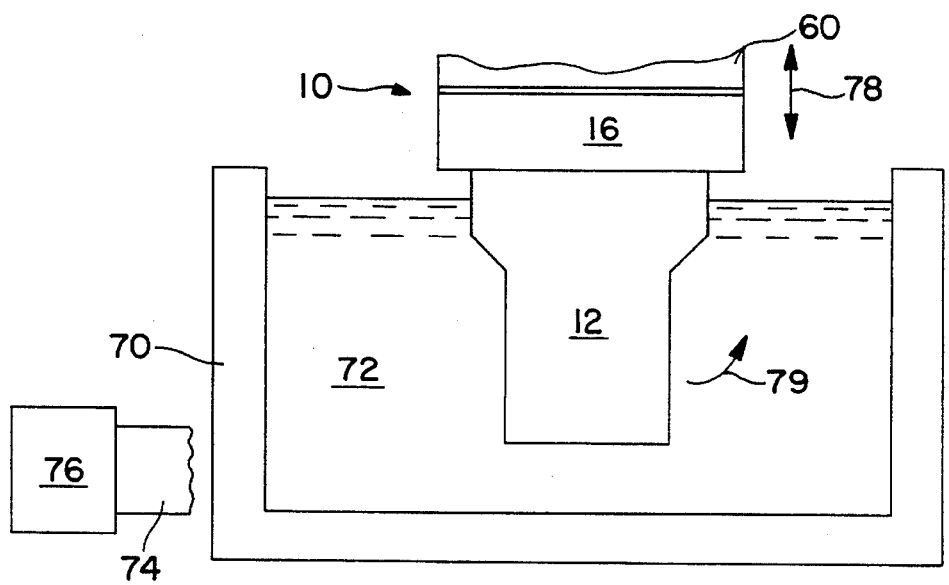
FIG. 1B is a schematic view of the test environment structure.

FIG. 1B shows the general mechanical environment of use of the instrument 10. A vessel 70 holds a thermal control fluid, normally water. But a higher temperature fluid may be used where high temperatures of the fluid being measured are required. Such high temperature of the fluid being measured may arise due to its high temperature as received in cup 12 and/or as imparted thereto by shearing rotation. Paraffin is a common example of such higher temperature fluid. A heater 74 and related power supply/controls 76 are provided. The vessel can be raised about the cup 12 after it is assembled to collar 16B and lowered for disassembly and changeover of test fluids or instrument maintenance or the instrument 10 can be lowered and raised into and out of bath 72 as indicated by arrow 78. Arrow 79 indicates cup rotation.

A shroud 60 surrounds the motor, gearing and rigid fixed structure and keeps the wire internal to the instrument except for a shielded cable (not shown) passing through a shroud opening. A power cable (not shown) for the motor also passes through a shroud opening.

One or more sleeve barriers 12-1 (FIG. 1) in the cup holder eliminates or minimizes the measurement significance of centrifugal force effects of fluid at a level above the significant measuring channel 13.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed:

1. Viscometer instrument comprising:
    (a) means for holding a fluid to be measured and means for driving the holder rotatably to impart shearing force to the fluid therein,
    (b) means defining a suspended spindle measuring element and suspension means therefor, the spindle element being suspended within the holding means for low angular deflection in response to forces transmitted via the fluid means for response impacting shearing drive of the fluid upon the spindle to pick up means a torque at the suspended spindle, the latter being concentrically and axially held via an elongated mount and having a torsional pickup movable through a small arc in linear response to the torque transferred via the fluid, and further comprising a transducer for converting such movement into an electrical output,
    (c) said means for imparting shearing drive comprising an elongated rotatable first hollow shaft mounted on a further second, fixed hollow shaft via axially spaced bearing means, the first shaft supporting the holding means at a position axially remote from the transducer means to substantially isolate the latter from the fluid being measured;
    (d) means defining a rigid readout wire mounted between the torsional pickup means and a rotor portion of the transducer element via a radial jewel bearing, said wire passing through but freely movable relative to said suspending means; and
    (e) means to pressurize fluid being tested, and further comprising means defining an effective annular measuring zone between pre-selected holder and spindle portions and for limiting the effect of fluid shear upon the transducer to said zone while substantially preventing an alteration of that effect due to fluid activity outside such zone.

2. The instrument of claim 1 wherein a seal is provided between the rotating holder means and the fixed shaft.

3. The instrument of claim 1 wherein the spindle and a portion of the holder are concentric over the measuring length of such zone and providing space above the fluid level therein to accommodate fluid, thermal expansion,
    the said means for limiting comprising baffle means suspended from said fixed hollow second shaft structure and disconnected from the rotating holder and angularly deflectable spindle structure and arranged at a position just above the said annular measuring zone to limit physical movement of fluid from the annulus and otherwise limit shear force transmission between the rotating holder and spindle outside the measuring zone.

4. The instrument of claim 1 wherein the elongated mount comprises a tube surrounding the torsion element and providing spindle alignment surfaces spaced significantly apart axially for accuracy and providing for rigid rotational coupling with the spindle and also accommodating a sealing of the spindle at an end remote from the measuring zone to minimize loss of volatiles into the body of the spindle.

* * * * *